United States Patent [19]

Cordier et al.

[11] Patent Number: 4,761,506
[45] Date of Patent: Aug. 2, 1988

[54] PROCESS FOR THE PREPARATION OF PERFLUOROALKANOLS

[75] Inventors: Georges Cordier, Francheville; Jean-Serge Ferlut, Lyons, both of France

[73] Assignee: Rhone-Poulenc Specialites Chimiques, Courbevoie, France

[21] Appl. No.: 30,265

[22] Filed: Mar. 24, 1987

Related U.S. Application Data

[63] Continuation of Ser. No. 780,376, Sep. 25, 1985, abandoned.

[30] Foreign Application Priority Data

Sep. 28, 1984 [FR] France .................. 84 145917

[51] Int. Cl.$^4$ .................................................. C07C 31/38
[52] U.S. Cl. .............................................................. 568/842
[58] Field of Search ............................................. 568/842

[56] References Cited

U.S. PATENT DOCUMENTS 2,824,897  2/1958  Wujciak et al. .
3,356,746 12/1967  Anello et al. .
3,356,747 12/1967  Anello et al. .
4,072,726  2/1978  Nychka et al. .
4,232,170 11/1980  Grey et al. .

FOREIGN PATENT DOCUMENTS 0036939 10/1981  European Pat. Off. .
2060357  6/1971  France .

Primary Examiner—Howard T. Mars
Attorney, Agent, or Firm—Finnegan, Henderson, Farabow, Garrett and Dunner

[57] ABSTRACT

A process is disclosed for the preparation of perfluoroalkanols by reacting an ester of a perfluorinated acid in the liquid phase with hydrogen under a pressure of between about 1 and 300 bars in the presence of a catalyst based on at least one metal selected from nickel, cobalt, copper and the metals of the platinum group. The perfluoroalkanols are employed as synthesis intermediates in the pharmaceutical and plant-protection industries.

22 Claims, No Drawings

PROCESS FOR THE PREPARATION OF PERFLUOROALKANOLS

This application is a continuation of application Ser. No. 180,376, filed Sept. 25, 1985, now abandoned.

BACKGROUND OF THE INVENTION

The present invention relates to a process for the preparation of perfluoroalkanols. More particularly, the present invention relates to a process for the preparation of perfluoroalkanols by hydrogenation of the corresponding perfluorinated esters.

It is known from U.S. Pat. Nos. 3,356,747 and 4,072,726 to prepare perfluoroalkanols from perfluorinated esters by vapor phase hydrogenolysis of the esters in the presence of a catalyst based either on a mixed oxide of chromium and copper or on Cu alone. This hydrogenolysis requires substantial heating of the reactants (200° to 350° C.), which results in production costs which are too high to allow consideration of industrial exploitation of the process.

It is also known, from the French patent published under No. 2,060,357, to prepare perfluoroalkanols by hydrogenolysis of perfluorinated esters in water in the presence of a mineral acid such as phosphoric acid. The disadvantage of using an aqueous phase is that in this case partial hydrolysis of the ester occurs, with formation of a perfluorinated acid which in water has a highly corrosive action on the apparatus. Accordingly, this process, for technical reasons, cannot be exploited industrially. It is also known from European Pat. No. 36,939 to prepare perfluoroalkanols by hydrogenolysis of the corresponding perfluorinated esters in the presence of a catalytic composition comprising a metal of group VIII, an alkali metal and an anion radical chosen from among arene radicals and aliphatic alkoxides, at a temperature of about 150° C. The presence of adjuvants such as the alkali metal and the anion radical adds greatly to the cost of production of the trifluoroethanol.

None of the previously described processes allows industrial exploitation, either because the technique is too expensive or because the apparatus can be corroded.

The present invention has succeeded in overcoming these problems and relates to a process for the preparation of perfluoroalkanols characterized in that an ester of a perfluorinated acid corresponding to the formula:

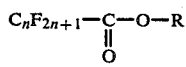
$$C_nF_{2n+1}-\underset{\underset{O}{\|}}{C}-O-R \qquad (I)$$

in which:
n is greater than or equal to 1; and
R is selected from alkyl, alkylphenyl, cycloalkyl, phenyl, halogenoalkyl, halogenoalkylphenyl, halogenocycloalkyl and halogenophenyl groups, optionally mixed with an ester of a nonperfluorinated acid of the formula:

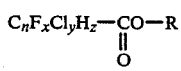
$$C_nF_xCl_yH_z-\underset{\underset{O}{\|}}{CO}-R \qquad (II)$$

in which:
n is an integer greater than or equal to 1;
x is an integer between 0 and 2n;
y is an integer between 0 and 2n+1;
z is an integer between 0 and 2n+1;
the sum of x+y+z is equal to 2n+1; and
R has the same meaning as in formula (I), is brought into contact, in the liquid phase, with hydrogen at a total pressure of between about 1 and 300 bars in the presence of a catalyst based on at least one metal selected from nickel, cobalt, copper and the metals of the platinum group.

In formulas (I) and (II), n is preferably equal to or greater than 1 and equal to or less than 12.

In the R substituent in formulas (I) and (II), "alkyl" preferably has from 1 to 6 carbon atoms, more preferably from 1 to 4 carbon atoms, "cycloalkyl" preferably has from 4 to 7 ring carbon atoms, more preferably from 5 to 6 ring carbon atoms, and "halogens" is selected from chloro, fluoro, iodo and bromo and is preferably fluoro.

Representative compounds of formula (I) include ethyltrifluoroacetate, phenyltrifluoroacetate and trifluoroethyl trifluoroacetate. It is preferred to use compounds of formula (I) in which R represents a 1,1-dihydroperfluoroalkane group and more preferably a $-CH_2-C_nF_{2n+1}$ group.

The perfluorinated acid ester preferred according to the invention is trifluoroethyl trifluoroacetate.

The catalyst employed according to the process of the invention may be selected from catalysts based on metals of the platinum group, defined herein as ruthenium, rhodium, iridium, platinum and palladium.

The catalyst of the invention may also include nickel, cobalt and copper. According to a preferred embodiment of the invention, the nickel, cobalt and copper are of the Raney type.

The catalysts used in the present invention may be employed in the metallic state, in the form of an oxide or a salt such as, for example, the chromites or in the form of a mixture of these states. Moreover, they may or may not be deposited on a carrier. Any carrier which is inert under the reaction conditions, such as charcoal, silica or alumina, may be employed. The use of charcoal is very especially preferred.

Among the catalysts, a catalyst based on ruthenium or on rhodium is preferably used. This catalyst is preferably deposited on charcoal.

Preferably, use is made of a quantity of metal, deposited on a carrier, which is less than about 20% by weight, preferably between about 1 and 10% by weight and, more preferably, about 5% by weight, based on the weight of the carrier.

The quantity of catalyst, expressed as the weight of metal employed, is preferably less than about 10% by weight, more preferably from about 1 to 10% by weight, based on the weight of the perfluorinated acid ester. In the case of metals of the platinum group, use is more preferably made of less than about 2% of metal and, more preferably, of less than about 1% of metal, based on the weight of the perfluorinated acid ester. In the case of Raney nickel, use is preferably made of between about 1 and 5% by weight of metal, based on the weight of the perfluorinated acid ester.

The process is preferably carried out at a temperature between the ambient temperature and about 300° C. and more preferably between about 80° and 150° C.

A total pressure of between about 5 and 150 bars is advantageous for carrying out the invention and a pressure of between about 15 and 50 bars is preferred.

The reaction can in particular take place in the presence of solvents which are inert to hydrogenation, such as alkanols, cycloalkanols, alkanes, cycloalkanes, ethers and non-fluorinated esters. As examples of such solvents there may be mentioned trifluoroethanol, cyclohexanol, diisopropyl ether, petroleum cuts corresponding to alkanes of about 6 to 12 carbon atoms and esters of acetic acid such as the acetate of secondary butanol. If the reaction is carried out in the presence of a solvent, it is preferred to use trifluoroethanol, but in the case of the more volatile esters the reaction is preferably carried out without a solvent.

Moreover, when an ester of a perfluorinated acid obtained by, for example, incomplete fluorination of the corresponding perchlorinated acid and containing products corresponding to the general formula (II) is employed, the process makes it possible to avoid the formation of non-perfluorinated alcohols such as, for example, monofluoroethanol, which has an extremely high toxicity even at very low doses. In fact, during the hydrogenation in the presence of the catalysts according to the invention, the esters of non-perfluorinated acids of formula (II) are completely converted to hydrofluoric acid, hydrochloric acid and non-toxic organic compounds.

The acids formed have the effect of slowing down the hydrogenation reaction. Thus, to avoid this adverse effect, a base is advantageously added. If the reaction takes place in the absence of a solvent or in the presence of organic solvents, it is preferred to add an organic base selected from the tertiary amines and the quaternary ammonium hydroxides. The reaction can take place in the presence of an amount of water of which the molar ratio relative to the ester is less than about 10%, and this allows the addition of an inorganic base such as sodium hydroxide, potassium hydroxide, lithium hydroxide and a carbonate. In such a case, it is preferred to add sodium hydroxide or potassium hydroxide.

The invention is particularly indicated for the preparation of trifluoroethanol by hydrogenation of trifluoroethyl trifluoroacetate. Trifluoroethanol is used as a synthetic intermediate in the pharmaceutical and plant protection industries.

The invention will now be described more completely with the aid of the examples which follow which, however, are not to be regarded as limiting the invention.

EXAMPLE 1

TrifluoroethYl trifluoroacetate in an amount of 20 g and 0.8 g of a ruthenium catalyst deposited in an amount of 5% by weight on charcoal were charged into a Hastelloy $B_2$ 125 cm$^3$ autoclave. The air present in the autoclave was purged with nitrogen and the nitrogen was in turn removed by means of hydrogen. The autoclave was brought to a hydrogen pressure of 100 bars and was heated to 100° C. Reaction was allowed to proceed for 3 hours while maintaining this temperature and a total pressure of 100 bars. Analysis of the liquid phase showed that the degree of conversion of the trifluoroethyl trifluoroacetate was 98% and the yield of trifluoroethanol was 95%.

EXAMPLE 2

This example was carried out in the same apparatus and in accordance with the process described in Example 1, but in the presence of 18 g of trifluoroethyl trifluoroacetate and 0.3 g of a rhodium catalyst deposited in an amount of 5% on charcoal, and under the following reaction conditions:
total pressure: 19 bars of hydrogen
temperature: 90° C.
reaction time: 6 hours.

The resulting degree of conversion of the trifluoroethyl trifluoroacetate was 95% and the trifluoroethanol yield was 96%.

EXAMPLE 3

This example was carried out in the same apparatus and in accordance with the process described in Example 1, but in the presence of 18 g of trifluoroethyl trifluoroacetate and 0.3 g of a rhodium catalyst deposited in an amount of 5% on charcoal, and under the following reaction conditions:
total pressure: 50 bars of hydrogen
temperature: 90° C.
reaction time: 4 hours.

The resulting degree of conversion of the trifluoroethyl trifluoroacetate was 97% and the trifluoroethanol yield was 96%.

EXAMPLE 4

This example was carried out in the same apparatus and in accordance with the process described in Example 1, but in the presence of 18 g of trifluoroethyl trifluoroacetate and 0.3 g of a ruthenium catalyst deposited in an amount of 5% on charcoal, and under the following reaction conditions:
total pressure: 15 bars
temperature: 90° C.
time: 16 hours 30 minutes.

The resulting degree of conversion of the trifluoroethyl trifluoroacetate was 100% and the trifluoroethanol yield was 89%.

EXAMPLE 5

This example was carried out in the same apparatus and in accordance with the process described in Example 1, but in the presence of 12 g of trifluoroethyl trifluoroacetate and 0.5 g of an iridium catalyst deposited in an amount of 5% on charcoal, and under the following reaction conditions:
total pressure: 100 bars
temperature: 100° C.
time: 6 hours.

The resulting degree of conversion of the trifluoroethyl trifluoroacetate was 96% and the trifluoroethanol yield was 90%.

EXAMPLE 6

This example was carried out in the same apparatus and in accordance with the process described in Example 1, but in the presence of 12 g of trifluoroethyl trifluoroacetate and 0.5 g of a platinum catalyst deposited in an amount of 5% on charcoal, and under the following reaction conditions:
total pressure: 100 bars
temperature: 100° C.
time: 15 hours.

The resulting degree of conversion of the trifluoroethyl trifluoroacetate was 90% and the trifluoroethanol yield was 94%.

EXAMPLE 7

This example was carried out in the same apparatus and in accordance with the process described in Example 1, but in the presence of 43 g of trifluoroethyl trifluoroacetate and 1.92 g of a palladium catalyst deposited in an amount of 10% on charcoal, and under the following reaction conditions:
total pressure: 100 bars
temperature: 150° C.
time: 21 hours.

The resulting degree of conversion of the trifluoroethyl trifluoroacetate was 45% and the trifluoroethanol yield was 92%.

EXAMPLE 8

This example was carried out in the same apparatus and in accordance with the process described in Example 1, but in the presence of 18 g of ethyl trifluoroacetate and 1.6 g of a ruthenium catalyst deposited in an amount of 5% on charcoal, and under the following reaction conditions:
total pressure: 100 bars
temperature: 150° C.
time: 5 hours.

The resulting degree of conversion of the ethyl trifluoroacetate was 100% and the trifluoroethanol yield was 89%.

EXAMPLE 9

This example was carried out in the same apparatus and in accordance with the process described in Example 1, but in the presence of 18 g of ethyl trifluoroacetate and 1.6 g of an iridium catalyst deposited in an amount of 5% on charcoal, and under the following reaction conditions:
total pressure: 100 bars
temperature: 150° C.
time: 5 hours.

The resulting degree of conversion of the ethyl trifluoroacetate was 30% and the trifluoroethanol yield was 97%.

EXAMPLE 10

This example was carried out in the same apparatus and in accordance with the process described in Example 1, but in the presence of 37 g of phenyl trifluoroacetate and 1.92 g of a rhodium catalyst deposited in an amount of 5% on charcoal, and under the following reaction conditions:
total pressure: 100 bars
temperature: 90° C.
time: 15 hours 30 minutes The resulting degree of conversion of the phenyl trifluoroacetate was 100% and the trifluoroethanol yield was 98%.

EXAMPLE II

This example was carried out in the same apparatus and in accordance with the process described in Example 1, but in the presence of 33 g of cyclohexyl trifluoroacetate and 1.92 g of a rhodium catalyst deposited in an amount of 5% on charcoal, and under the following reaction conditions:
total pressure: 100 bars
temperature: 100° C.
time: 22 hours 30 minutes.

The resulting degree of conversion of the cyclohexyl trifluoroacetate was 100% and the trifluoroethanol yield was 91%.

What is claimed is:

1. A process for the preparation of trifluoroethanol which comprises bringing an ester of a trifluorinated acid of the formula (I):

in which R is selected from alkyl, alkylphenyl, cycloalkyl, phenyl, halogenoalkyl, halogenoalkylphenyl, halogenocycloalkyl and halogenophenyl groups, alone or mixed with an ester of a non-perfluorinated acid of the formula (II):

in which
x is an integer between 0 and 2,
y is an integer between 0 and 3,
z is an integer between 0 and 3,
the sum of x+y+z is equal to 3, and
R has the same meaning as in formula (I), into contact, in the liquid phase, with hydrogen at a total pressure of between about 1 and 300 bars in the presence of a catalyst consisting of a metal deposited on an inert carrier, said metal being present in an amount less than 20% by weight based on the weight of said carrier, wherein said metal is in the metallic form, the form of a metal oxide, the form of a metal chromite, or is a mixture thereof, and wherein said metal is selected from the group consisting of platinum, rhodium and ruthenium, and wherein said ester of formula (II), when present, is completely converted to hydrofluoric acid, hydrochloric acid and non-toxic organic compounds,
with the proviso that said contact is conducted in the absence of water, except that when an ester of formula (II) is present and an inorganic base is added to be present during said contact step, said inorganic base is dissolved in an amount of water such that the molar ratio of water to ester is less than about 0.1.

2. The process according to claim 1, wherein in formula (I) R is a b 1,1-dihydroperfluoroalkane group.

3. The process according to claim 1 wherein in formula (I) R is a radical which corresponds to the formula —$CH_2$—$C_nF_{2n+1}$ in which n is an integer equal to or greater than 1.

4. The process according to claim 1, wherein said ester of a trifluorinated acid is trifluoroethyl trifluoroacetate.

5. The process according to claim 4, wherein said catalyst consists of a metal deposited on an inert carrier selected from the group consisting of charcoal, silica and alumina.

6. The process according to claim 1, wherein said catalyst consists of a metal in the metallic form deposited on said inert carrier.

7. The process according to claim 1, wherein said metal is selected from the group consisting of ruthenium and rhodium and said inert carrier is charcoal.

8. The process according to claim 1 wherein from about 1 to 10% by weight of catalyst, expressed as metal based on the trifluorinated acid ester, is employed.

9. The process according to claim 1 wherein the reaction temperature is between the ambient temperature and 300° C.

10. The process according to claim 9 wherein the reaction temperature is between about 80° and 150° C.

11. The process according to claim 1 wherein the total pressure is between atmospheric pressure and about 250 bars.

12. The process according to claim 11, wherein the total pressure is between about 5 and 150 bars.

13. The process according to claim 1 wherein said process is carried out in the presence of a solvent.

14. The process according to claim 13 wherein the solvent is trifluoroethanol.

15. The process according to claim 1 wherein, when the compound of formula II is present, a base is added.

16. The process according to claim 15 wherein the base is selected from the group consisting of organic and inorganic bases.

17. The process of claim 1, wherein the degree of conversion of said ester of the formula (I) is at least 90%.

18. The process of claim 4, wherein the degree of conversion of said trifluoroethyl trifluoroacetate is at least 90%.

19. The process of claim 1, wherein the yield of said trifluoroethanol is 89 to 98%.

20. The process of claim 4, wherein the yield of said trifluoroethanol is 89 to 96%.

21. The process according to claim 1, wherein an ester of the formula (II) is mixed with an ester of the formula (I).

22. The process according to claim 1, wherein said metal is selected form rhodium and platinum and is present in an amount of about 5% by weight, based on the weight of the carrier.

* * * * *

UNITED STATES PATENT AND TRADEMARK OFFICE
CERTIFICATE OF CORRECTION

PATENT NO.   :   4,761,506

DATED        :   August 2, 1988

INVENTOR(S)  :   GEORGES CORDIER and JEAN-SERGE FERLUT

It is certified that error appears in the above-identified patent and that said Letters Patent is hereby corrected as shown below:

Title page, under Foreign Application Priority Data, change "84 145917" to -- 84 14917 --.

Signed and Sealed this

Twenty-fourth Day of January, 1989

*Attest:*

DONALD J. QUIGG

*Attesting Officer*     *Commissioner of Patents and Trademarks*